United States Patent
Lui et al.

(10) Patent No.: US 8,766,012 B2
(45) Date of Patent: Jul. 1, 2014

(54) PROCESS FOR THE PREPARATION OF 2,2-DIFLUOROETHYLAMINE STARTING FROM PROP-2-EN-1-AMINE

(75) Inventors: Norbert Lui, Odenthal (DE); Christian Funke, Leichlingen (DE); Jens-Dietmar Heinrich, Burscheid (DE); Thomas Norbert Müller, Monheim (DE)

(73) Assignee: Bayer Cropscience AG, Monheim (DE)

( * ) Notice: Subject to any disclaimer, the term of this patent is extended or adjusted under 35 U.S.C. 154(b) by 447 days.

(21) Appl. No.: 13/292,765

(22) Filed: Nov. 9, 2011

(65) Prior Publication Data

US 2012/0142971 A1 Jun. 7, 2012

Related U.S. Application Data

(60) Provisional application No. 61/413,059, filed on Nov. 12, 2010.

(30) Foreign Application Priority Data

Nov. 12, 2010 (EP) .................................. 10191059

(51) Int. Cl.
*C07C 211/00* (2006.01)
*C07C 209/00* (2006.01)
*C07C 209/08* (2006.01)
*C07C 211/20* (2006.01)
*C07C 211/21* (2006.01)
*C07C 211/15* (2006.01)

(52) U.S. Cl.
CPC ............. *C07C 209/08* (2013.01); *C07C 211/15* (2013.01); *C07C 211/20* (2013.01); *C07C 211/21* (2013.01)
USPC ............................ 564/510; 564/509; 564/486

(58) Field of Classification Search
CPC .. C07C 209/08; C07C 211/15; C07C 211/20; C07C 211/21
USPC .......................................... 564/486, 509, 510
See application file for complete search history.

(56) References Cited

U.S. PATENT DOCUMENTS

| 4,030,994 A | 6/1977 | Kollonitsch |
| 5,773,617 A | 6/1998 | Bernard et al. |

OTHER PUBLICATIONS

International Search Report of PCT/EP2011/069546 Dated Nov. 30, 2011.

*Primary Examiner* — Jafar Parsa
(74) *Attorney, Agent, or Firm* — Miles and Stockbridge

(57) ABSTRACT

A process for the preparation of 2,2-difluoroethylamine of the formula (I)

$$CHF_2CH_2NH_2 \quad (I)$$

comprising the stages (i) and (ii):
stage (i): reaction of 2,2-difluoro-1-haloethane of the formula (II)

$$CHF_2—CH_2Hal \quad (II)$$

in which Hal is chlorine, bromine or iodine,
with prop-2-en-1-amine of the formula (III)

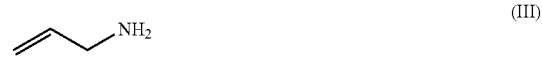

to give N-(2,2-difluoroethyl)prop-2-en-1-amine of the formula (IV)

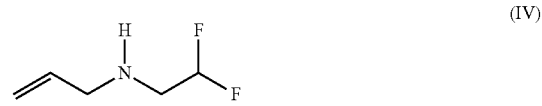

preferably in the presence of an acid scavenger,
and
stage (ii): removal of the allyl group from the N-(2,2-difluoroethyl)prop-2-en-1-amine of the formula (IV) obtained in stage (i) to give 2,2-difluoroethylamine of the formula (I) or a salt thereof.

20 Claims, No Drawings

PROCESS FOR THE PREPARATION OF 2,2-DIFLUOROETHYLAMINE STARTING FROM PROP-2-EN-1-AMINE

CROSS REFERENCE TO RELATED APPLICATIONS

This application claims priority to European application 10191059.4 filed Nov. 12, 2010 and U.S. provisional application 61/413,059 filed Nov. 12, 2010 the entire contents of which are incorporated herein by reference in their entireties.

BACKGROUND

1. Field of the Invention

The present invention relates to a process for the preparation of 2,2-difluoroethylamine by reaction of prop-2-en-1-amine with 2,2-difluoro-1-haloethane.

2. Description of Related Art 2,2-Difluoroethylamine is an important intermediate in the preparation of active substances. Various methods for the preparation of 2,2-difluoroethylamine are known.

Donetti et al. (J. Med. Chem., 1989, 32, 957-961) describe the synthesis of 2,2-difluoroethylamine hydrochloride starting from 2,2-difluoroacetamide. In this connection, the desired amine is prepared with a diborane solution in tetrahydrofuran (THF). The yield is 48%.

Kluger et al. (JACS, 1982, 104, 10, 2891-2897) describe the synthesis of 2,2-difluoroethylamine starting from the amide with sodium borohydride and boron trifluoride etherate. The yield is 60%. Vyazkov, V. A. et al. (Vyazkov, V. A., Gontar, A. F., Grinevskaya, V. K., Igoumnova, E. V. and Igoumnov, S. M., A. N.) Nesmeyanov Institute of Organoelement Compounds, Russian Academy of Sciences, Moscow, Russia Fluorine Notes (2009), 65) likewise describe the reduction with sodium borohydride in a yield of 50-65%.

In addition, Kollonitsch (U.S. Pat. No. 4,030,994) describes a synthesis of 2,2-difluoroethylamine, namely the reaction of ethylamine with fluoroxytrifluoromethane in hydrogen fluoride under UV radiation.

In a paper with a title "Über einige fluorhaltige Alkylamine" [On some fluorine-comprising alkylamines] (Chem. Zentralblatt, Volume 75, 1904, pages 944-945), Swarts describes the preparation of 2,2-difluoroethylamine and of tetrafluoroethylamine, with subsequent separation of the two products by fractional distillation or as hydrochloride or oxalate salts, after prior conversion of the products obtained. Swarts uses 1-bromo-2,2-difluoroethane as starting compound and heats this over a relatively long period of time, namely 3 days, in the reactor tube with 2 mol of alcoholic ammonia at relatively high temperatures, namely 125-145° C. The starting compound is completely converted into the compounds difluoroethylamine and tetrafluoroethylamine.

The preparation of 2,2-difluoroethylamine is also described by Dickey et al. (Industrial and Engineering Chemistry, 1956, No. 2, 209-213). 2,2-Difluoro-1-chloroethane is there reacted with 28% ammonium hydroxide, i.e. 28% aqueous ammonia solution, in an autoclave (rocking autoclave). The reaction mixture is heated at temperatures of 135° C. to 140° C. for 31 hours. After the reaction has ended, the reaction mixture is filtered and the amine is distilled off from the reaction mixture. However, since a lot of ammonia and some water are still found in the distillate, the amine is dried over sodium hydroxide and again distilled. The amine was thus obtained in a yield of 65%.

This process is disadvantageous as it requires, just as the process according to Swarts, a very long reaction time of 31 hours and the yield of 65% is rather low. At the same time, the reaction mixture is highly corrosive since the aqueous ammonia, in combination with the chloride and fluoride ions present in the reaction mixture, attacks metallic materials at the high temperatures used in the process.

All these known processes are disadvantageous, in particular because they cannot be carried out on an economically useful commercial (industrial) scale. The low yield and the use of expensive and dangerous chemicals, such as, e.g., sodium borohydride/$BF_3$ or diborane, prevent the processes according to Donetti et al. and Kluger et al. from being suitable for the commercial-scale preparation of 2,2-difluoroethylamine. The process according to Kollonitsch et al. uses dangerous chemicals and pure 2,2-difluoroethylamine is not obtained. The process according to Dickey et al. and the process according to Swarts are likewise unsuitable or uneconomic for commercial-scale use as they require very long reaction times and are at the same time non-selective, so that the yields of the processes are unsatisfactory.

Furthermore, the use of ammonia at high temperatures is problematic, since special pressure-resistant equipment is required, which is demanding and expensive from a safety viewpoint.

Starting from the known processes for the preparation of 2,2-difluoroethylamine, the question now arises of how 2,2-difluoroethylamine can be prepared in a simple and inexpensive way. The term "inexpensive processes" is understood to mean those processes which can be carried out without large financial expenditure because the starting materials, for example, are not dangerous, no other technical problems emerge, for example because the reaction mixture acts corrosively, and/or the desired 2,2-difluoroethylamine is obtained in a satisfactorily high yield and purity, because, for instance, the reaction takes place largely selectively.

SUMMARY

A particularly advantageous process for the preparation of 2,2-difluoroethylamine has now been found with which the abovementioned disadvantages are avoided and which can be implemented in a simple way on a commercial scale. In the process according to the invention, in a first stage, a 2,2-difluoro-1-haloethane compound is selectively converted, under comparatively mild reaction conditions and in a comparatively short reaction time, to the desired N-(2,2-difluoroethyl)prop-2-en-1-amine. In a second stage, the allyl group is again removed using a catalyst and the desired 2,2-difluoroethylamine is correspondingly obtained.

A subject-matter of the invention is accordingly a process for the preparation of 2,2-difluoroethylamine of the formula (I)

$$CHF_2CH_2NH_2 \qquad (I)$$

which comprises the following stages (i) and (ii):

stage (i)—alkylation: reaction of 2,2-difluoro-1-haloethane of the formula (II)

$$CHF_2—CH_2Hal \qquad (II),$$

in which Hal is chlorine, bromine or iodine, preferably chlorine or bromine and very preferably chlorine, with prop-2-en-1-amine of the formula (III)

to give N-(2,2-difluoroethyl)prop-2-en-1-amine of the formula (IV)

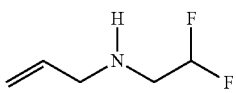
(IV)

preferably in the presence of an acid scavenger,
and
stage (ii): removal of the allyl group (deallylation) from the N-(2,2-difluoroethyl)prop-2-en-1-amine of the formula (IV) obtained in stage (i), through which 2,2-difluoroethylamine of the formula (I) or a salt thereof is obtained, preferably in the presence of a catalyst and optionally in the presence of a nucleophile.

DETAILED DESCRIPTION OF A PREFERRED EMBODIMENT

The process according to the invention can be illustrated by the following scheme:

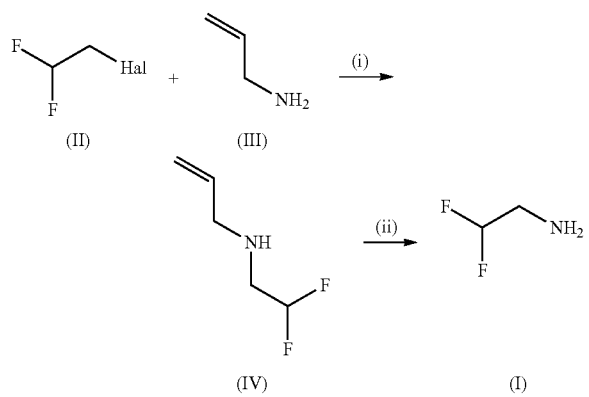

The desired 2,2-difluoroethylamine is obtained, with the process according to the invention, with good yields, with short reaction times and in high purity, which is why it is generally unnecessary to extensively work up the actual reaction product.

A subject-matter of the invention is likewise the process of the stage (i) for the preparation of N-(2,2-difluoroethyl)prop-2-en-1-amine, comprising the reaction of 2,2-difluoro-1-chloroethane with prop-2-en-1-amine in the presence of an acid scavenger and optionally in the presence of a catalyst, which comprises the process stages, reaction conditions and reactants described for stage (i).

A subject-matter of the invention is furthermore the use of N-(2,2-difluoroethyl)prop-2-en-1-amine in the preparation of 2,2-difluoroethylamine which comprises the process stages, reaction conditions and reactants described for stage (ii).

Although it is known, from M. Hudlicky in "Chemistry of Organofluorine Compounds", 2nd edition, 1976, pp. 489-490, and Houben Weyl, E 10b/2, pp. 92-98, that 2,2-difluoro-1-haloethane reacts under basic conditions with elimination of HHal (HCl, HBr or HI) to give vinylidene fluoride and is accordingly no longer available for the reaction in stage (i) and although it is known, from J. Org. Chem., 2007, 72(22), p. 8569, that 2,2-difluoroethylamines are very reactive and it is very probable that the N-(2,2-difluoroethyl)prop-2-en-1-amine of the formula (IV) obtained will react further under the reaction conditions in the stage (i), the Inventors have found, surprisingly, that N-(2,2-difluoroethyl)prop-2-en-1-amine of the formula (IV) is obtained by stage (i) of the process according to the invention in good yield and good purity, so that an extensive purification can be dispensed with. At the end of the day, the target compound 2,2-difluoroethylamine is accordingly also obtained in a very good yield, based on the starting materials used in the stage (i).

With regard to the alkylation in the stage (i), the inventors have found, contrary to the expectation that double or multiple alkylations will increasingly occur, that, if the sum of the molar amounts of reacting prop-2-en-1-amine of the formula (III) (allylamine) and acid scavenger is less than the molar amount of 2,2-difluorohaloethane of the formula (II) used, very high yields are achieved. If allylamine is used both as starting material and as acid scavenger, it is also the case here that the sum of the molar amount of allylamine which is reacted and the molar amount of allylamine which acts as scavenger is lower than the molar amount of 2,2-difluorohaloethane of the formula (II) used.

In the process according to the invention, use is preferably made of 2,2-difluoro-1-haloethane compounds of the formula (II) in which Hal is chlorine or bromine. Use is particularly preferably made of the compound 2,2-difluoro-1-chloroethane (CHF2-CH2Cl).

Prop-2-en-1-amine of the formula (III) (allylamine) is known and available commercially.

Unless otherwise specified, the term "alkyl", in isolation or in combination with other terms, such as, for example, alkoxy, refers to linear or branched saturated hydrocarbon chains with up to 12 carbon atoms, i.e. C1-C12-alkyl, preferably with up to 6 carbon atoms, i.e. C1-C6-alkyl, particularly preferably with up to 4 carbon atoms, i.e. C1-C4-alkyl. Examples of such alkyls are methyl, ethyl, n-propyl, isopropyl, n-butyl, isobutyl, s-butyl, t-butyl, n-pentyl, n-hexyl, n-heptyl, n-octyl, n-nonyl, n-decyl, n-undecyl and n-dodecyl. The alkyls can be substituted with a suitable substituent, e.g. with halogen.

Unless otherwise specified, "halogen" or "Hal" is fluorine, chlorine, bromine or iodine.

The reaction of 2,2-difluoro-1-haloethane of the formula (II) with prop-2-en-1-amine from stage (i) can be carried out neat, i.e. without addition of a solvent, or in the presence of a solvent.

In the event that a solvent is added to the reaction mixture in stage (i), it is preferably used in such an amount that the reaction mixture remains satisfactorily stirrable during the entire process. Use is advantageously made, based on the volume of the 2,2-difluoro-1-haloethane used, of the solvent in an amount of 1 to 50 times, preferably in an amount of 2 to 40 times and particularly preferably in an amount of 2 to 20 times. The term "solvent" is also understood to mean, according to the invention, mixtures of pure solvents. All organic solvents which are inert under the reaction conditions are suitable solvents. Suitable solvents according to the invention are in particular water, ethers (e.g., ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, diethylene glycol dimethyl ether, triethylene glycol dimethyl ether, tetrahydrofuran, 2-methyltetrahydrofuran, dioxane, and ethylene oxide and/or propylene oxide polyethers); compounds such as tetrahydrothiophene dioxide and dimethyl sulphoxide, tetramethylene sulphoxide, dipropyl sulphoxide, benzyl methyl sulphoxide, diisobutyl sulphoxide, dibutyl sulphoxide or diisoamyl sulphoxide; sulphones, such as dimethyl, diethyl, dipropyl, dibutyl, diphenyl, dihexyl, methyl ethyl, ethyl propyl, ethyl isobutyl and pentamethylene sulphone; aliphatic, cycloaliphatic or aromatic hydrocarbons (e.g., pentane, hexane, heptane, octane, nonane, such as white spirits with components with boiling points in the range, for example, from 40° C. to 250° C., cymene, benzine fractions within a boiling point interval from 70° C. to 190° C., cyclohexane, methylcyclohexane, petroleum ether, ligroin, benzene, toluene or xylene); halogenated aromatic compounds (e.g., chlorobenzene or dichlorobenzene); amides (e.g., hexamethyl-phosphoramide, formamide, N,N-dimethylacetamide, N-methylformamide, N,N-dimethylformamide, N,N-dipropylformamide, N,N-dibutylformamide, N-methylpyrrolidine, N-methylcaprolactam, 1,3-dimethyl-3,4,5,6-tetrahydro-2(1H)-pyrimidine, octylpyrrolidone, octylcaprolactam, 1,3-dimethyl-2-imidazolinedione, N-formylpiperidine or N,N'-1,4-diformylpiperazine); nitriles (e.g., acetonitrile, propionitrile, n-butyronitrile, isobutyronitrile or benzonitrile); ketones (e.g., acetone) or mixtures thereof.

Aromatic and/or aliphatic hydrocarbons, in particular toluene, N,N-dimethylacetamide, tetramethylene sulphoxide and N-methylpyrrolidone are preferred solvents in stage (i).

It is preferable according to the invention to carry out stage (i) neat, i.e. without solvent. The process can through this be carried out even more inexpensively, because the solvents do not have to be purchased or disposed of after reaction.

The reaction of the stage (i) is advantageously carried out in the presence of one or more acid scavengers which are able to bind the hydrogen halide compound (i.e. HCl, HBr or HI) released in the reaction. Acid scavengers are such compounds which are able to inactivate (neutralize) an acid.

All organic and inorganic bases which are able to bind the hydrogen halide compounds released are suitable acid scavengers. Examples of organic bases are tertiary nitrogen bases, such as, e.g., tertiary amines, substituted or unsubstituted pyridines and substituted or unsubstituted quinolines, triethylamine, trimethylamine, N,N-diisopropylethylamine, tri-n-propylamine, tri-n-butylamine, tri-n-hexylamine, tricyclohexylamine, N-methylcyclohexylamine, N-methylpyrrolidine, N-methylpiperidine, N-ethylpiperidine, N,N-dimethylaniline, N-methylmorpholine, pyridine, 2-, 3- or 4-picoline, 2-methyl-5-ethylpyridine, 2,6-lutidine, 2,4,6-collidine, 4-dimethylaminopyridine, quinoline, quinaldine, N,N,N,N-tetramethylethylenediamine, N,N-dimethyl-1,4-diazacyclohexane, N,N-diethyl-1,4-diazacyclohexane, 1,8-bis(dimethylamino)naphthalene, diazabicyclooctane (DABCO), diazabicyclononane (DBN), diazabicycloundecane (DBU), butylimidazole and methylimidazole.

Examples of inorganic bases are alkali metal or alkaline earth metal hydroxides, hydrogencarbonates or carbonates and other inorganic aqueous bases; preference is given, e.g., to sodium hydroxide, potassium hydroxide, lithium hydroxide, calcium hydroxide, sodium carbonate, potassium carbonate, sodium hydrogencarbonate, potassium hydrogencarbonate and sodium acetate.

The molar ratio of acid scavenger, in particular of abovementioned bases, to the prop-2-en-1-amine used lies in the range from approximately 0.1 to approximately 3, preferably in the range from approximately 0.5 to approximately 3 and particularly preferably in the range from approximately 0.7 to approximately 1.3. The use of larger amounts of base is technically possible but results in a loss in yield.

The molar ratio of 2,2-difluoro-1-haloethane to the prop-2-en-1-amine used normally lies in the range from approximately 30:1 to approximately 1:3, preferably in the range from approximately 10:1 to approximately 1:2 and particularly preferably in the range from approximately 8:1 to approximately 1:1.

In a preferred embodiment, the prop-2-en-1-amine acts as acid scavenger, so that no additional acid scavenger has to be added. In this case, the molar ratio of 2,2-difluoro-1-haloethane to the prop-2-en-1-amine used normally lies in the range from approximately 15:1 to approximately 1:3, preferably in the range from approximately 8:1 to approximately 1:2.5 and particularly preferably in the range from approximately 4:1 to approximately 1:2.

The prop-2-en-1-amine and the base can also be introduced into the 2,2-difluoro-1-haloethane of the formula (II).

Although stage (i) of the process according to the invention is generally carried out without addition of a catalyst, use may also be made, in stage (i), of catalysts which accelerate the reaction of the prop-2-en-1-amine with 2,2-difluorohaloethane. The reaction temperature is reduced by the use of a catalyst, by which the intrinsic pressure of the reaction mixture is also reduced. If the intrinsic pressure is not so high, the operation can be carried out under simpler conditions industrially.

Alkali metal bromides and iodides (e.g., sodium iodide, potassium iodide or potassium bromide); ammonium bromide and ammonium iodide; tetraalkylammonium bromides and iodides (e.g., tetraethylammonium iodide); certain phosphonium halides, such as tetraalkyl- or tetraarylphosphonium halides (e.g., hexadecyl(tributyl)phosphonium bromide, stearyltributylphosphonium bromide, tetrabutylphosphonium bromide, tetraoctylphosphonium bromide, tetraphenylphosphonium chloride and tetraphenylphosphonium bromide), tetrakis(dimethylamino)phosphonium bromide, tetrakis(diethylamino)phosphonium bromide and tetrakis (dipropylamino)phosphonium chloride and bromide, and bis (dimethylamino)[(1,3-dimethylimidazolidin-2-ylidene) amino]methylium bromide are suitable in particular according to the invention. Mixtures of suitable catalysts are also conceivable.

Of the abovementioned catalysts which can be used in stage (i), sodium iodide, potassium iodide, potassium bromide, tetrabutylammonium bromide and tetraphenylphosphonium bromide are particularly suitable for accelerating the reaction of the stage (i). Sodium iodide and potassium iodide are to be particularly emphasised.

The catalyst can also be produced in situ. For example, it can be produced by reaction of HBr or HI with ammonia or by addition of highly reactive alkyl bromides or iodides (e.g., methyl bromide, ethyl bromide, methyl iodide or ethyl iodide).

If a catalyst is present in the stage (i), it is used, based on the 2,2-difluoro-1-haloethane of the formula (II) used, in a concentration of approximately 0.01 to approximately 25% by weight. Higher concentrations are possible in principle. The catalyst is preferably used in a concentration of approximately 0.2 to approximately 25% by weight, particularly preferably of approximately 0.4 to approximately 20% by weight and very particularly preferably of approximately 0.5 to approximately 15% by weight. However, the catalyst can also preferably be used in a concentration of approximately 0.05 to approximately 3% by weight, of approximately 0.1 to approximately 10% by weight or of approximately 0.5 to approximately 10% by weight.

The reaction of the stage (i) is carried out in principle under intrinsic pressure in a pressure-resistant closed test vessel (autoclave). The pressure during the reaction (i.e., the intrinsic pressure) depends on the reaction temperature used, the 2,2-difluoro-1-haloethane used, the catalyst used and the amount of prop-2-en-1-amine. The pressure also likewise depends on the solvent used, if a solvent is present in the stage (i). If an increase in pressure is desired, an additional increase in pressure can be achieved by adding an inert gas, such as nitrogen or argon.

The reaction temperature in stage (i) can vary depending on the starting materials used. If no catalyst is added in the stage (i), stage (i) is carried out at internal temperatures (i.e., the temperature which is present in the reaction vessel) in the range from approximately 70° C. to approximately 200° C. It is preferable, in carrying out the reaction stage (i), for the internal temperature to lie in the range from approximately 90° C. to approximately 150° C., particularly preferably in the range from approximately 90° C. to approximately 140° C. It has been established that, if the operation is carried out in the preferred temperature range, few side reactions, in particular multiple alkylations, occur.

If a catalyst is used in stage (i), the reaction temperature of the reaction mixture is correspondingly reduced. It is well known to a person skilled in the art to what extent the reaction temperature is reduced on adding a certain catalyst and he can find the optimum reaction internal temperature range for the specific reaction mixture from routine experiments or from his knowledge and from the abovementioned internal temperature ranges.

The reaction time of the reaction in stage (i) lies in the range from approximately 0.5 to approximately 20 hours. A longer reaction time is possible but is not useful economically.

The reaction mixture from stage (i) is worked up either by filtration and subsequent fractional distillation or by diluting (addition of water in which optionally salts are dissolved) the reaction mixture, subsequent phase separation and subsequent fractional distillation. The base or the prop-2-en-1-amine can be rereleased by an additional base, e.g. sodium hydroxide solution, and correspondingly fed back again into the process.

The N-(2,2-difluoroethyl)prop-2-en-1-amine of the formula (IV) prepared in stage (ii) is then subjected to the deallylation of the stage (ii), i.e. the allyl group in N-(2,2-difluoroethyl)prop-2-en-1-amine of the formula (IV) is removed (cleaved off).

It is preferable for the deallylation to take place in the presence of a catalyst.

Methods for the cleaving of an allylic C—N bond are well known and are described, for example, in the review by Stephanie Escoubet, Stephane Gastaldi and Michele Bertrand in European Journal of Organic Chemistry (2005), (18), pages 3855-3873. With regard to carrying out the stage (ii), reference is extensively made here to these methods. The "Tsuji-Trost reaction" is likewise a deallylation. It is the palladium-catalysed allylation of nucleophiles, such as C-acid compounds, enolates, amines and phenols, with allyl compounds, such as allyl acetates or allyl bromides.

The deallylation can be carried out by isomerisation of the double bond of the allyl group to give an enamine, which then can be cleaved by hydrolysis (reaction route (2) in Scheme 7), or the allyl group can be transferred to an anionic nucleophile (Nu) and the 2,2-difluoroethylamine be released (reaction route (1) in Scheme 7).

Scheme 7:

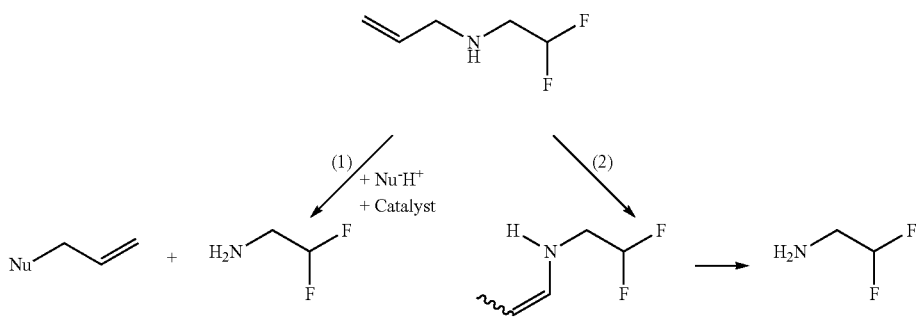

If the deallylation takes place as represented in Scheme 7 according to reaction route (2), then an acid for the cleaving of the enamine has to be present in stage (ii). Examples of such acids are methanesulphonic acid, p-toluenesulphonic acid, formic acid and acetic acid. The reaction conditions for cleaving the allyl group are to be chosen so that the 2,2-difluoroethylamine formed is stable; in particular, no strong bases are used for the rearrangement since losses of product otherwise occur. Strong bases are those bases in which the equilibrium reaction lies completely on the side of the OH⁻ ions.

In a preferred embodiment of the stage (ii), the removal of the allyl group from N-(2,2-difluoroethyl)prop-2-en-1-amine takes place in the presence of a suitable catalyst. Suitable catalysts are heterogeneous or homogeneous catalysts which comprise one or more metals from Groups 8-10 of the Periodic Table. The corresponding catalysts can also be used in supported form, for example applied to carbon (charcoal or active charcoal), aluminium oxide, barium sulphate, barium carbonate, silicon dioxide, zirconium dioxide, calcium carbonate or titanium dioxide. Suitable metals are in particular noble metals (e.g., ruthenium, palladium, platinum and rhodium). Palladium(II) chloride, palladium(II) acetate, bis (acetylacetonate)palladium(II), dichlorobis(triphenylphosphine)palladium(II), tetrakis(triethylphosphine)palladium, tetrakis(triphenylphosphine)palladium and ruthenium(III) chloride are suitable as homogeneous catalysts. Preference is given to palladium(0) catalysts, in particular 10% palladium-on-charcoal. Palladium(II) chloride, palladium(II) acetate, bis(acetylacetonate)palladium(II), dichlorobis(triphenylphosphine)palladium(II), tetrakis(triethylphosphine) palladium and tetrakis(triphenylphosphine)palladium are likewise suitable. The catalysts can be used both in their water-moistened form and in their dry form.

If the deallylation of the stage (ii) takes place in the presence of a catalyst, then the catalyst is used, based on the compound of the formula (IV) used, in a concentration of approximately 0.001 to approximately 20 mol %. The catalyst is preferably used in a concentration of approximately 0.01 to approximately 10 mol %, particularly preferably of approximately 0.01 to approximately 5.0 mol %.

If the deallylation of the stage (ii) takes place in the presence of a catalyst, it is then advantageous for a compound to be present which acts as nucleophile. Typical compounds which act as nucleophiles and accordingly are called nucleophiles are anionic nucleophiles, such as hydroxides, alkoxides, thiolates, carbanions, halides, peroxides, cyanides and azides. The anionic nucleophiles can be used in protonated form. Such protonated nucleophiles are, e.g., thiols, sulphinic acids, 2-mercaptobenzoic acid, malonic acid and the derivatives thereof, and β-dicarbonyl compounds, barbituric acids, such as N,N'-dimethylbarbituric acid, or amines, such as ethanolamine.

It is generally advantageous to carry out stage (ii) in the presence of a solvent (diluent) or solvent mixture. Solvents are advantageously used in such an amount that the reaction mixture remains satisfactorily stirrable during the deallylation. All organic solvents which are inert under the reaction conditions are possible as solvents for carrying out stage (ii), the type of the solvent used depending on the type of the deallylation.

Mention may be made, as examples, of alcohols, such as methanol, ethanol, isopropanol or butanol; ethers, such as ethyl propyl ether, methyl tert-butyl ether, n-butyl ether, anisole, phenetole, cyclohexyl methyl ether, dimethyl ether, diethyl ether, dimethyl glycol, diphenyl ether, dipropyl ether, diisopropyl ether, di-n-butyl ether, diisobutyl ether, diisoamyl ether, ethylene glycol dimethyl ether, isopropyl ethyl ether, tetrahydrofuran, methyltetrahydrofuran, dioxane, dichlorodiethyl ether, and ethylene oxide and/or propylene oxide polyethers; amines, such as trimethyl-, triethyl-, tripropyl- or tributylamine, N-methylmorpholine, pyridine, alkylated pyridines and tetramethylenediamine; aliphatic, cycloaliphatic or aromatic hydrocarbons, such as pentane, n-hexane, n-heptane, n-octane, nonane and technical-grade hydrocarbons which can be substituted by fluorine and chlorine atoms, such as dichloromethane, trichloromethane, carbon tetrachloride, fluorobenzene, chlorobenzene or dichlorobenzene; cyclohexane, methylcyclohexane, petroleum ether, ligroin, octane, benzene, toluene, chlorobenzene, bromobenzene, nitrobenzene or xylene; esters, such as methyl, ethyl, butyl or isobutyl acetate, and dimethyl, dibutyl or ethylene carbonate; water; organic acids, such as formic acid, acetic acid, trifluoroacetic acid or propionic acid, and inorganic acids, such as sulphuric acid, hydrochloric acid or phosphoric acid.

Of the abovementioned solvents, water, ethanol and butanol are preferred.

After the end of the deallylation, the 2,2-difluoroethylamine obtained can be purified by distillation. Alternatively, the 2,2-difluoroethylamine can also be isolated and purified as salt, e.g. hydrochloride. The salt is produced by addition of acid, before, during or after the deallylation. The salt can subsequently be rereleased by addition of base.

However, the 2,2-difluoroethylamine usually has such a purity that it can be further used in the solvent after filtration of the catalyst.

The present invention is more fully described from the following examples, without the invention by this being limited to these.

PREPARATION EXAMPLES

1. Preparation of N-(2,2-difluoroethyl)prop-2-en-1-amine (step (i))

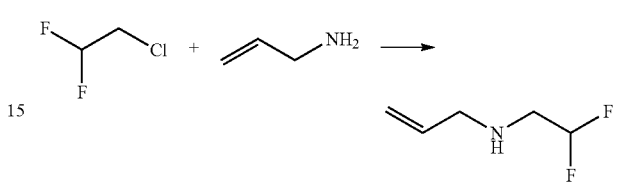

Example 1.1

An amount of 382 g (3.67 mol) of 2,2-difluoro-1-chloroethane and 70 g (1.2 mol) of prop-2-en-1-amine are heated in an autoclave at 120° C. for 16 hours. The reaction mixture is treated with 200 g of water and the phases are subsequently separated. The organic phase is distilled at 55° C. An amount of 65 g of N-(2,2-difluoroethyl)prop-2-en-1-amine is obtained (corresponds to 87.4% yield, based on reacted prop-2-en-1-amine). Unreacted prop-2-en-1-amine, which precipitates as hydrochloride, can be rereleased by addition of sodium hydroxide solution.

$^1$H NMR (CDCl$_3$): 5.76-6.0 (m, 2H), 5.22 (m, 1H), 3.31 (m, 2H), 2.96 (dt, 2H)

Example 1.2

An amount of 382 g (3.67 mol) of 2,2-difluoro-1-chloroethane and 70 g of prop-2-en-1-amine (1.2 mol) are heated in an autoclave at 120° C. for 16 hours. The crude mixture is subsequently filtered and the residue is washed with 150 g of 2,2-difluoro-1-chloroethane. The organic phase is first distilled at standard pressure and 55° C. Residual amounts of 2,2-difluoro-1-chloroethane are removed at 500 mbar and the residue is finely distilled under vacuum. An amount of 56 g of N-(2,2-difluoroethyl)prop-2-en-1-amine is obtained (corresponds to 76% yield). Unreacted prop-2-en-1-amine, which precipitates as hydrochloride, can be rereleased by addition of sodium hydroxide solution.

$^1$H NMR (CDCl$_3$): 5.76-6.0 (m, 2H), 5.22 (m, 1H), 3.31 (m, 2H), 2.96 (dt, 2H)

2. Preparation of 2,2-difluoroethylamine (State (ii)—deallylation)

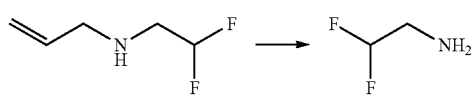

Example 2.1

An amount of 50 g (0.404 mol) of N-(2,2-difluoroethyl) prop-2-en-1-amine is dissolved in 253 g (4.1 mol) of 2-aminoethanol and treated with 2.5 g (1.2 mmol) of 10% palladium-on-charcoal (water-moistened). The mixture is subsequently heated at 90° C. The product produced, 2,2-difluoroethylamine, is then distilled off under vacuum at 100 mbar and 50° C. internal temperature. The distillate is again finely distilled. An amount of 23 g of 2,2-difluoroethylamine is obtained (corresponds to 68% yield).

$^1$H NMR (CDCl$_3$): 5.5-5.9 (m, 1H), 2.94-3.1 (m, 2H), 1.26 (br m, NH$_2$)

The invention claimed is:

1. A process for the preparation of 2,2-difluoroethylamine of formula (I)

CHF$_2$CH$_2$NH$_2$      (I)

and/or a salt thereof
comprising the stages (i) and (ii):
stage (i): reaction of 2,2-difluoro-1-haloethane of formula (II)

CHF$_2$—CH$_2$Hal      (II)

in which Hal is chlorine, bromine or iodine,
with prop-2-en-1-amine of formula (III)

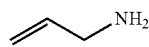

(III)

to give N-(2,2-difluoroethyl)prop-2-en-1-amine of formula (IV)

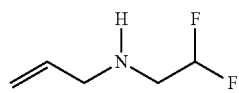

(IV)

optionally in the presence of an acid scavenger,
and
stage (ii): removal of the allyl group from the N-(2,2-difluoroethyl)prop-2-en-1-amine of the formula (IV) obtained in stage (i), through which 2,2-difluoroethylamine of the formula (I) and/or a salt thereof is obtained.

2. The process according to claim 1, in which stage (ii) is carried out in the presence of a catalyst comprising at least one metal from Groups 8-10 of the Periodic Table and optionally in the presence of a nucleophile, the nucleophile being at least one selected from the group consisting of hydroxides, alkoxides, thiolates, carbanions, halides, peroxides, cyanides and azides, thiols, sulphinic acids, 2-mercaptobenzoic acid, malonic acid and the derivatives thereof, and β-dicarbonyl compounds, barbituric acids, N,N'-dimethylbarbituric acid, amines and ethanolamine.

3. The process according to claim 2, in which the catalyst is a palladium catalyst.

4. The process according to claim 3, in which the catalyst is selected from the group consisting of palladium(0) catalysts, 10% palladium-on-charcoal, palladium(II) chloride, palladium(II) acetate, bis(acetylacetonate)palladium(II), dichlorobis(triphenylphosphine)palladium(II), tetrakis(triethylphosphine)palladium and tetrakis(triphenylphosphine) palladium.

5. The process according to claim 1, in which a portion of the prop-2-en-1-amine used acts as said acid scavenger, while another portion of the prop-2-en-1-amine used is reacted.

6. The process according to claim 1, in which, in stage (i), an organic or inorganic base is used as said acid scavenger.

7. The process according to claim 1, in which stage (i) is carried out without solvent.

8. The process according to claim 1, in which stage (i) is carried out in the presence of a catalyst which is at least one selected from the group consisting of alkali metal bromides and iodides, ammonium bromide, ammonium iodide, tetraalkylammonium bromides, tetraalkylammonium iodides, tetraalkylphosphonium halides, tetraarylphosphonium halides, tetrakis(dimethyl-amino)phosphonium bromide, tetrakis(diethylamino)phosphonium bromide, tetrakis(dipropylamino)phosphonium chloride, tetrakis(dipropylamino) phosphonium chloride, and -bromide, and bis (dimethylamino)[(1,3-dimethylimidazolidin-2-ylidene) amino]-methylium bromide.

9. The process according to claim 1, in which, in formula (II), Hal is chlorine.

10. A process for the preparation of N-(2,2-difluoroethyl) prop-2-en-1-amine, comprising reacting 2,2-difluoro-1-chloroethane with prop-2-en-1-amine in the presence of an acid scavenger and optionally in the presence of a catalyst.

11. N-(2,2-difluoroethyl)prop-2-en-1-amine which is capable of being used in the preparation of 2,2-difluoroethylamine, comprising the removal of the allyl group by deallylation.

12. The process according to claim 2, in which a portion of the prop-2-en-1-amine used acts as said acid scavenger, while another portion of the prop-2-en-1-amine used is reacted.

13. The process according to claim 3, in which a portion of the prop-2-en-1-amine used acts as said acid scavenger, while another portion of the prop-2-en-1-amine used is reacted.

14. The process according to claim 4, in which a portion of the prop-2-en-1-amine used acts as said acid scavenger, while another portion of the prop-2-en-1-amine used is reacted.

15. The process according to claim 2, in which, in stage (i), an organic or inorganic base is used as said acid scavenger.

16. The process according to claim 3, in which, in stage (i), an organic or inorganic base is used as said acid scavenger.

17. The process according to claim 4, in which, in stage (i), an organic or inorganic base is used as said acid scavenger.

18. The process according to claim 5, in which, in stage (i), an organic or inorganic base is used as said acid scavenger.

19. The process according to claim 2, in which stage (i) is carried out without solvent.

20. The process according to claim 3, in which stage (i) is carried out without solvent.

* * * * *